United States Patent [19]

Roger et al.

[11] Patent Number: 5,383,878
[45] Date of Patent: Jan. 24, 1995

[54] SURGICAL SCREW

[75] Inventors: Gregory J. Roger; Leo A. Pinczewski, both of Crows Nest, Australia

[73] Assignee: Hip Developments Pty Ltd., Crows Nest, Australia

[21] Appl. No.: 39,056
[22] PCT Filed: Aug. 30, 1991
[86] PCT No.: PCT/AU91/00405
§ 371 Date: Apr. 5, 1993
§ 102(e) Date: Apr. 5, 1993
[87] PCT Pub. No.: WO92/03980
PCT Pub. Date: Mar. 19, 1992

[30] Foreign Application Priority Data

Sep. 4, 1990 [AU] Australia ................ PK2119

[51] Int. Cl.⁶ ............... A61B 17/58; F16B 35/06
[52] U.S. Cl. ................... 606/73; 606/75; 606/72
[58] Field of Search .............. 606/72, 73, 75, 76, 606/77

[56] References Cited

U.S. PATENT DOCUMENTS

| | | | |
|---|---|---|---|
| 2,242,003 | 5/1941 | Lorenzo | 128/92 |
| 2,267,925 | 12/1941 | Johnston | 128/92 |
| 4,463,753 | 8/1984 | Gustilo | 128/92 |
| 4,537,185 | 8/1985 | Stednitz | 128/92 B |
| 4,744,793 | 5/1988 | Parr et al. | 623/13 |
| 4,870,957 | 10/1989 | Goble et al. | 128/92 YF |
| 4,927,421 | 5/1990 | Goble et al. | 606/73 |
| 4,950,270 | 8/1990 | Bowman et al. | 606/72 |
| 5,084,050 | 1/1992 | Draenert | 606/73 |
| 5,116,337 | 5/1992 | Johnson | 606/73 |
| 5,129,906 | 7/1992 | Ross et al. | 606/77 |

FOREIGN PATENT DOCUMENTS

| | | |
|---|---|---|
| 14615/28 | 7/1928 | Australia . |
| 59999/90 | 2/1991 | Australia . |
| 0172130 | 2/1986 | European Pat. Off. . |
| 0241792 | 10/1987 | European Pat. Off. . |
| 0282789 | 9/1988 | European Pat. Off. . |
| 0317406 | 5/1989 | European Pat. Off. . |
| 0374088 | 6/1990 | European Pat. Off. . |
| 0451932 | 10/1991 | European Pat. Off. . |
| 2622790 | 5/1989 | France . |
| 2818254 | 10/1979 | Germany . |
| WO89/09030 | 10/1989 | WIPO . |
| WO90/08510 | 8/1990 | WIPO . |

OTHER PUBLICATIONS

European Patents Abstracts, Week 9240, p. 235, EP 506420-A1.
European Patents Abstracts, Week 9240, p. 189, EP 506213-A1.
European Patents Abstracts, Week 9237, p. 161, EP 502698-A1.
European Patents Abstracts, Week 9212, p. 267, EP 475-889-A.
European Patents Abstracts, Week 9208, p. 99, EP 471-419-A.
European Patents Abstracts, Week 9206, p. 99, EP 469-441-A.

(List continued on next page.)

Primary Examiner—Stephen C. Pellegrino
Assistant Examiner—Sonya C. Harris
Attorney, Agent, or Firm—Jacobson, Price, Holman & Stern

[57] ABSTRACT

A surgical screw has a head being, at least in a portion, hemispherical. A smooth continuous join exists between the head and a shank of the screw, the head being of the same, or larger, diameter as the shank. To drive the screw a drive socket is provided concentrically within the head, and a cannulation is provided concentrically of the shank and it opens into the socket so as to allow the screw to be threaded along a guide wire or similar. The shank has a smooth or soft thread so as to provide an interlocking fixation of a bone end of a tendon graft within a prepared hole of a bone, but without damaging either bone structures. The hemispherical portion provides a smooth continuous curved surface over which a graft may flex and move without fatigue or suffering stress concentrations.

6 Claims, 2 Drawing Sheets

OTHER PUBLICATIONS

European Patents Abstracts, Week 9144, p. 250 EP 454–601–A.

European Patents Abstracts, Week 9143, p. 28, EP 452–442–A.

European Patents Abstracts, Week 9106, p. 29, EP 411–109–A.

European Patents Abstracts, Week 9118, p. 74, EP 424–734–A.

European Patents Abstracts, Week 9133, p. 77, EP 440–991–A.

European Patents Abstracts, Week, 9133, EP 441–065 A.

European Patents Abstracts, Week 9134, p. 177, EP 442–629–A.

SURGICAL SCREW

BACKGROUND ART

This invention relates to surgical screws which are particularly well adapted for securing Patellar Tendon Grafts during reconstruction of the Anterior Cruciate Ligament.

Damaged Anterior Cruciate Ligaments can be repaired by grafting a Patellar Tendon physiologically bound to blocks of bone at each end, between the femur and tibia within the knee joint. The graft is inserted into a prepared hole and initially bound by a screw inserted within the hole beside the graft bone. After time the graft fuses with the bone material. While this technique works generally well problems can occur in that the head of the screw rests against the graft material and, as the knee is bent and the graft swings around, the head of the screw acts as a fulcrum for the graft and can damage the graft fibres. Other problems can occur in that conventional screw threads will cut into, and therefore damage, the graft. Also conventional screws can, in some procedures, be lost into the knee joint cavity causing a longer than necessary operation and further trauma.

DISCLOSURE OF THE INVENTION

According to one broad form, the present invention provides a surgical screw having a shank with a thread formed along the shank, the thread, in longitudinal section along the entirety of the thread, being devoid of an outermost cutting line, and a head with a generally hemispherical head portion of a diameter equal to that of the shank proximate the head or having a greater such diameter and another head portion of equal diameter tapering smoothly from the outer periphery of the first head portion down to the shank.

BRIEF DESCRIPTION OF DRAWINGS

By way of example only, one preferred embodiment of the invention will now be described with reference to the drawings in which.

BEST MODE OF CARRYING OUT INVENTION

Figure 1:
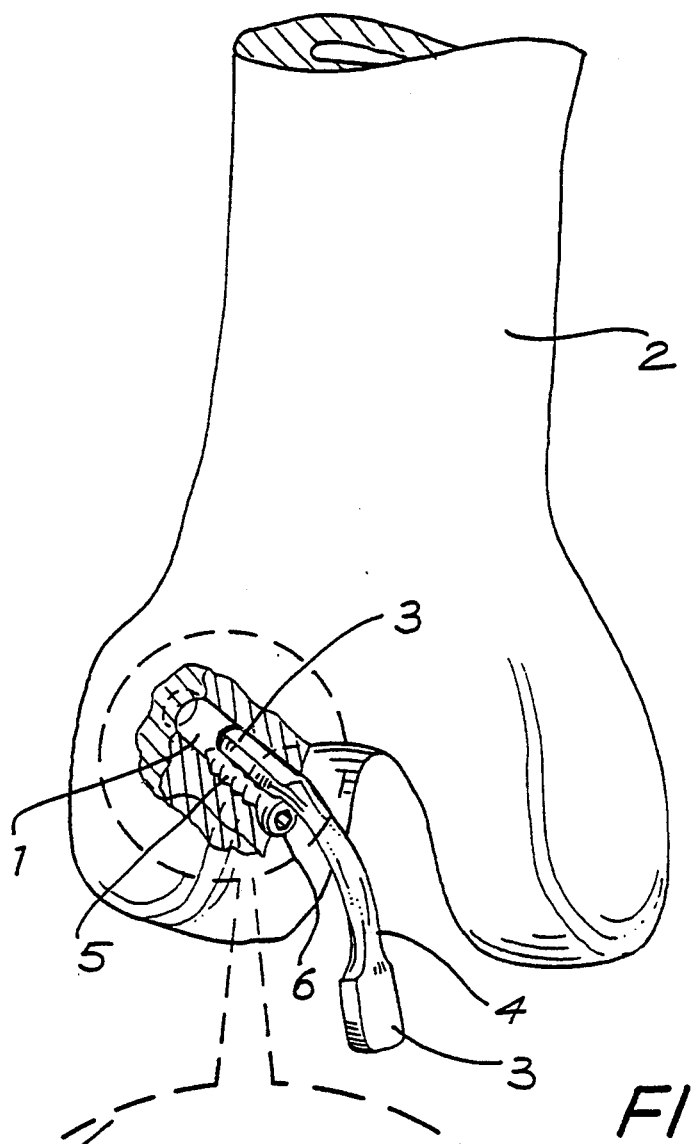
FIG. 1 is a schematic representation of the knee joint end of a femur in which a screw according to the invention has been inserted.
Figure 1:
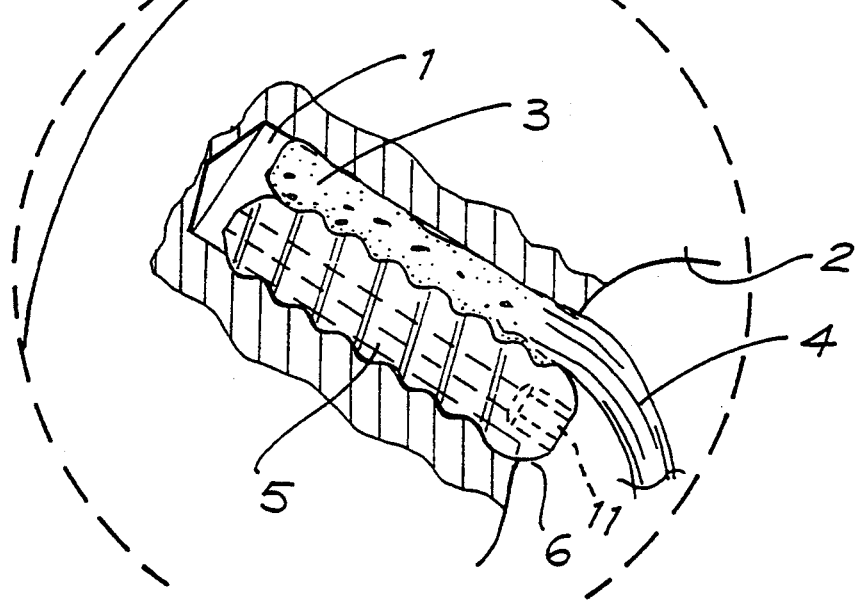

When repairing damaged Anterior Cruciate Ligaments, a blind hole 1 is drilled into the knee joint section of the femur 2 and a bone end 3 of a Patellar Tendon Graft 4 is inserted into the hole 1 where it is secured in place by driving in a screw 5. The screw head 6 lies generally under the Tendon Graft 4 and thus, once the knee is again put into normal use, the Tendon Graft 4 will be led over the screw head 6 and there will be some mutual movement between the two.

Figure 2:
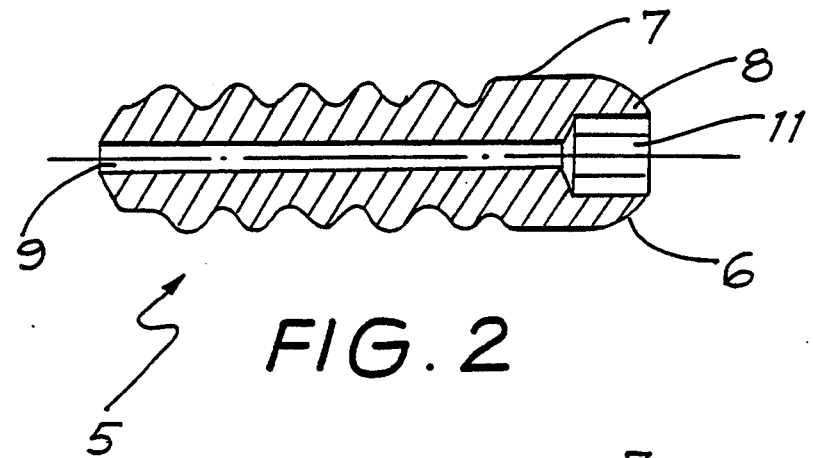
FIG. 2 is a schematic sectional view of a screw incorporating the present invention.

Although the screw 5 should not actually cut the bone 3 of the Tendon Graft 4, it must interlock its thread portions with both the bone 3 and inside wall of the hole 1 in order to maintain bone 3 rigidly positioned for the necessary period of time for it to fuse to the femur 2. Thus, as seen in FIG. 2 the thread form of the screw 5 is sinusoidal in longitudinal section, that is, it has no outermost cutting line which would normally helically follow the thread crest.

The screw head 6 has a surface which extends smoothly and continuously from the general shank 7 into a hemispherical end portion 8. Central of the head 6, and aligned with the longitudinal axis of the screw 5, is a hexagonal socket 11 for accepting a mating hexagonal drive to screw the screw 5 into its position. The radius of the hemispherical end portion 8 will generally be in the order of 4 mm as the typical screw for this operation will be of an overall diameter of 8 mm, or thereabouts.

Figure 3:
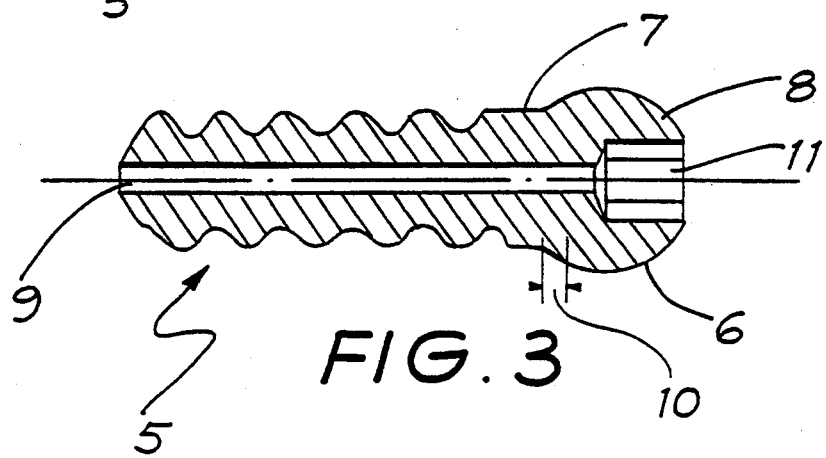
FIG. 3 is a view, similar to FIG. 2, of a modified embodiment of the invention.
Figure 4:
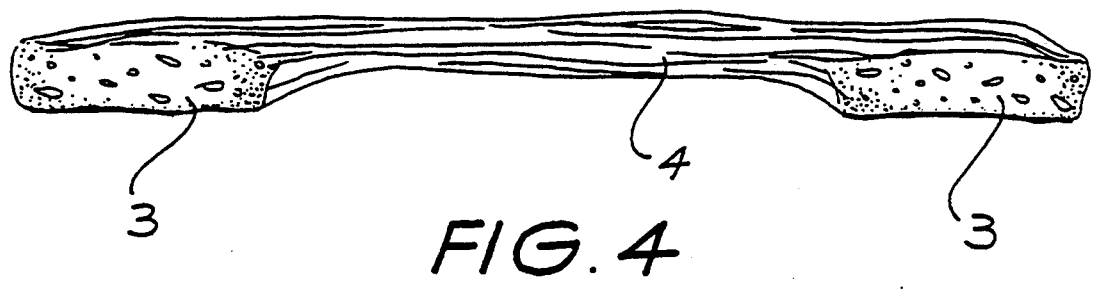
FIG. 4 is a schematic representation of the Patellar Tendon Graft which may be anchored using a screw such as that shown in FIG. 2.

As shown in FIG. 3, the head portion 8 may also be of greater diameter than the screw shank 7, the head portion being a greater part-sphere with a smooth transition to a frusto-conical collar 10 tapering down to the shank 7.

Of course, the screw 5 may be used in other operative situations where a screw of significantly different diameter is preferred, the head 6 will generally remain approximately hemispherical with a smooth transition to the shank.

In order to more easily lead and align the screw 5 as it is first inserted into hole 1, a central cannulation 9 is included along the length of the screw 5. The cannulation 9 allows the screw to be handled by a large diameter Kirschener wire, or similar, thus the diameter of cannulation 9 would typically be in the order of 2.4 mm.

I claim:

1. A surgical screw having a shank with a longitudinal axis, a thread extending along a length of the shank from one end of the shank, the thread being devoid of an outer cutting line throughout said length, a head at tan opposite end of the shank, said head having an outer surface extending smoothly and continuously from an adjacent part of the shank, said outer surface including a hemispherical end portion having a diameter at least equal to a maximum diameter of said part of the shank, and a recess in the head for an insertion tool.

2. A surgical screw as claimed in claim 1, wherein said part of the shank is unthreaded and wherein the diameter of said surface is equal to the maximum diameter of said part of the shank.

3. A surgical screw as claimed in claim 1, wherein the diameter of said surface is greater than the maximum diameter of said part of the shank and said surface tapers down to the shank through a frusto-conical transition zone.

4. A surgical screw as claimed in claim 1, wherein the thread is substantially sinusoidal as viewed in a plane passing through the longitudinal axis of the shank.

5. A surgical screw as claimed in claim 1, which includes a canulation extending along the longitudinal axis of the shank and through said recess.

6. A surgical screw as claimed in claim 1, in which said surface has a diameter of about 4 mm.

* * * * *

UNITED STATES PATENT AND TRADEMARK OFFICE
CERTIFICATE OF CORRECTION

PATENT NO. : 5,383,878
DATED : January 24, 1995
INVENTOR(S) : Gregory J. Roger and Leo A. Pinczewski It is certified that error appears in the above-indentified patent and that said Letters Patent is hereby corrected as shown below:

Column 2, line 44, after "a" insert —substantially—; after "portion" insert —having a curved surface remote from the shank—.

Column 2, line 45, after "said" insert —adjacent—.

Column 2, line 48, after "said" insert —adjacent—.

Signed and Sealed this

Fifteenth Day of August, 1995

Attest:

BRUCE LEHMAN

Attesting Officer   Commissioner of Patents and Trademarks

(12) REEXAMINATION CERTIFICATE (4425th)

United States Patent
Roger et al.

(10) Number: US 5,383,878 C1
(45) Certificate Issued: Aug. 28, 2001

(54) SURGICAL SCREW

(75) Inventors: Gregory J. Roger; Leo A. Pinczewski, both of Crows Nest (AU)

(73) Assignee: Smith & Nephew, Inc., Memphis, TN (US)

Reexamination Request:
No. 90/005,729, May 17, 2000

Reexamination Certificate for:
Patent No.: 5,383,878
Issued: Jan. 24, 1995
Appl. No.: 08/039,056
Filed: Apr. 5, 1993

Certificate of Correction issued Aug. 15, 1995.

(22) PCT Filed: Aug. 30, 1991
(86) PCT No.: PCT/AU91/00405
§ 371 Date: Apr. 5, 1993
§ 102(e) Date: Apr. 5, 1993
(87) PCT Pub. No.: WO92/03980
PCT Pub. Date: Mar. 19, 1992

(30) Foreign Application Priority Data

Sep. 4, 1990 (AU) .................................................. PK2119

(51) Int. Cl.[7] ........................... A61B 17/58; A61B 17/86; F16B 35/06
(52) U.S. Cl. ................................. 606/73; 606/72; 606/75
(58) Field of Search .................................................. 606/73

(56) References Cited

U.S. PATENT DOCUMENTS 3,103,926 * 9/1963 Cochran et al. ........................ 606/73
4,468,200 * 8/1984 Munch ................................... 606/73
4,537,185 * 8/1985 Stednitz ................................ 606/73

FOREIGN PATENT DOCUMENTS 27 47 312 A1 4/1999 (DE) ....................................... 606/73

* cited by examiner

*Primary Examiner*—Paul J. Hirsch

(57) ABSTRACT

A surgical screw has a head being, at least in a portion, hemispherical. A smooth continuous join exists between the head and a shank of the screw, the head being of the same, or larger, diameter as the shank. To drive the screw a drive socket is provided concentrically within the head, and a cannulation is provided concentrically of the shank and it opens into the socket so as to allow the screw to be threaded along a guide wire or similar. The shank has a smooth or soft thread so as to provide an interlocking fixation of a bone end of a tendon graft within a prepared hole of a bone, but without damaging either bone structures. The hemispherical portion provides a smooth continuous curved surface over which a graft may flex and move without fatigue or suffering stress concentrations.

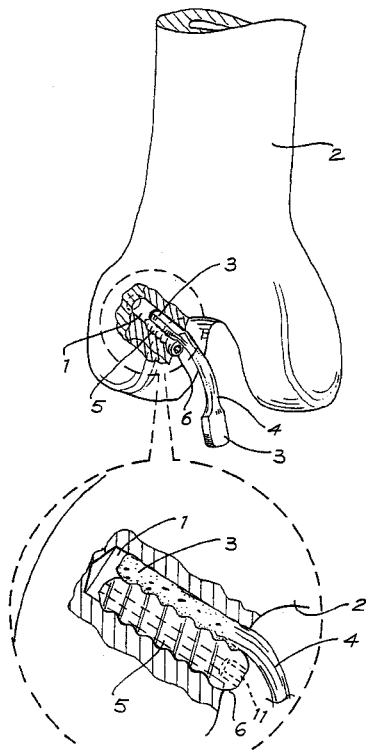

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2–6, dependent on an amended claim, are determined to be patentable.

1. A surgical screw having a shank with a longitudinal axis, a thread extending along a length of the shank from one end of the shank, the thread being devoid of an outer cutting line throughout said length, a head at [tan] *an* opposite end of the shank, said head having an outer surface extending smoothly and continuously from an adjacent part of the shank, said outer surface including a substantially hemispherical end portion having a curved surface remote from the shank having a diameter at least equal to a maximum diameter of said adjacent part of the shank, and a recess in the head for an insertion tool.

* * * * *